United States Patent [19]
Cordier et al.

[11] Patent Number: 5,856,577
[45] Date of Patent: Jan. 5, 1999

[54] PROCESS FOR THE PREPARATION OF FLUOROANILINES FROM FLUORINATED NITRATED BENZENE COMPOUNDS

[75] Inventors: Georges Cordier, Francheville; Gilbert Guidot, Caluire et Cuire; Philippe Marion, Villeurbanne; Claude Mercier, Lyons, all of France

[73] Assignee: Rhone-Poulenc Chimie, Courbevoie, France

[21] Appl. No.: 849,144

[22] PCT Filed: Nov. 29, 1995

[86] PCT No.: PCT/FR95/01575

§ 371 Date: May 28, 1997

§ 102(e) Date: May 28, 1997

[87] PCT Pub. No.: WO96/16926

PCT Pub. Date: Jun. 6, 1996

[30] Foreign Application Priority Data

Nov. 30, 1994 [FR] France ................................. 94/14395
Dec. 30, 1994 [FR] France ................................. 94/15956

[51] Int. Cl.⁶ ........................ C07C 209/36; C07C 211/52
[52] U.S. Cl. ............................. 564/412; 564/417
[58] Field of Search ..................... 564/412, 417

[56] References Cited

U.S. PATENT DOCUMENTS

| 5,294,742 | 3/1994 | Schach | 564/417 |
| 5,629,449 | 5/1997 | Albright | 564/417 |

FOREIGN PATENT DOCUMENTS 0 001 825 10/1978 European Pat. Off.
0 562 435 3/1993 European Pat. Off.

OTHER PUBLICATIONS

Database WPI, Week 8231, Derwent Publications Ltd., London, GB; AN 82–63760e & DD–A–154 214 (VEB Leuna–Werk W Ulrich), Mar. 3, 1982 abrege.

Chemical Abstracts, vol. 120, No. 19, May 9, 1994, Columbus, Ohio, US; Abstract No. 244212h, Mason, James et al. 'Synthesis of 2,4–difluoroaniline and 1,3–difluorobenzene from 1,2,4–trichlorobenzen' p. 956; col. 2,; "abrege" & Synth. Commun., vol. 24, No. 4, 1994 pp. 529–532.

Copy of Preliminary International Search Report PCT/FR95/01575 (Mar. 1996).

*Primary Examiner*—Richard L. Raymond
*Attorney, Agent, or Firm*—Katherine L. Carleton; Jean-Louis Seugnet

[57] ABSTRACT

The instant invention relates to a process for the preparation of fluoroanilines of formula (I) wherein a fluorinated nitrated benzene compound of formula (II) is subjected to a catalytic hydrogenation in a liquid medium containing a catalyst, under hydrogen pressure, carrying out a catalytic reduction reaction and, optionally, a hydrogenolysis reaction, wherein the compound of formula (II) is introduced gradually into the said medium so that the content of compound of formula (II) in the liquid remains less than or equal to 1000 ppm by mass, in order selectively to form the compound of formula (I).

24 Claims, No Drawings

PROCESS FOR THE PREPARATION OF FLUOROANILINES FROM FLUORINATED NITRATED BENZENE COMPOUNDS

The present invention relates to a process for the preparation of fluoroanilines, in particular of difluoroanilines, from optionally substituted fluorinated nitrated benzene compounds.

Fluoroanilines are synthetic precursors which are of very particular interest in the field of medicaments and plant protection.

However, they are not prepared directly but result from multistage synthetic processes, which makes these products very expensive. With the aim of reducing the cost price of these compounds, it is advisable to use stages in which the yields are as high as possible, in particular the final stage.

The various synthetic processes proposed for arriving at fluoroanilines involve fluorinated nitrated compounds which are subsequently reduced to amines. A specific access route comprises the preparation of a fluorinated, and generally chlorinated, nitrobenzene, in order subsequently to subject it to a hydrogenation operation in order to reduce the nitro functional group to an amine functional group, while hydrogenolysing the possible chlorine atoms, which are thus replaced by hydrogen atoms.

Thus, U.S. Pat. No. 4,140,719 describes a synthesis of 2,4-difluoroaniline involving the hydrogenation of 5-chloro-2,4-difluoronitrobenzene, with a yield of 84%.

Likewise, U.S. Pat. No. 5,294,742 describes the hydrogenation of 2,6-dichloro-3,5-difluoronitrobenzene, to give 3,5-difluoroaniline with a yield of 88.9%.

Such yields are acceptable in the laboratory but imply a certain loss of profit, which it would be advisable to avoid in the light of an industrial application.

In addition, it is to be noted that these yields are accompanied by quantitative degrees of conversion, the remainder of the starting material being converted into compounds of azo or azoxy type but also, as has been found by the present Inventors, into polyanilines by polycondensation, these by-products being regarded as highly toxic. Their presence, even as traces after purification, is thus a major disadvantage for the purpose of the use of the fluoroanilines in the synthesis of medicaments or of products which are in contact with the environment (in particular in products for agriculture).

Thus, the aim of the present invention is to provide a process for the preparation of fluoroanilines, in particular of difluoroanilines, from fluorinated nitrated benzene compounds with a virtually quantitative yield, without significant formation of toxic by-products.

The aim of the invention is in particular to provide a process for the hydrogenation of such fluorinated nitrated benzene compounds which makes it possible to carry out the reduction of the said compounds and optionally the hydrogenolysis of halogen substituents, other than fluorine atoms, selectively with respect to hydrodefluorination.

To this effect, one object of the invention is a process for the preparation of a compound of formula (I)

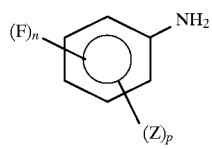

wherein n has a value from 1 to 5,
Z is a radical which is stable under catalytic hydrogenation conditions,
p is less than 5−n, according to which a compound of formula (II)

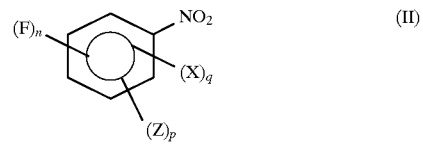

where n, Z and p have the above meanings,
X is a hydrogenolysable radical,
q has a value from 0 to 5−(n+p),
is subjected to a catalytic hydrogenation in a liquid medium containing a catalyst, under hydrogen pressure, carrying out a catalytic reduction reaction and, if appropriate, a hydrogenolysis reaction, characterized in that the compound of formula (II) is introduced gradually into the said medium so that the content of compound of formula (II) in the liquid remains less than or equal to 1000 ppm by mass, in order selectively to form the compound of formula (I).

The compounds where X represents a halogen atom, especially a chlorine atom, and especially chlorodifluoronitrobenzenes, are particularly targeted as starting compounds of formula (II).

The Z radical can be any hydrocarbon radical, optionally comprising at least one heteroatom, which is non-hydrogenolysable, that is to say which is not replaced by a hydrogen atom under catalytic hydrogenation conditions. Such a group can be in particular an alkyl group.

According to the invention, in order to obtain a good conversion and a good selectivity, and thus a good yield of the desired product, the compound of formula (II) is gradually introduced into the hydrogenation medium, so that the content of compound of formula (II) in the reaction liquid remains less than or equal to 1000 ppm, preferably less than or equal to 500 ppm, in particular in the range from 200 to 500 ppm.

The gradual introduction, non-continuously or continuously, of the benzene compound into the hydrogenation medium makes it possible to avoid, in a noteworthy way, the formation of undesirable by-products.

Preferably, the nitrated benzene compound is introduced continuously into the hydrogenation medium.

This introduction must be carried out so that the content of compound of formula (II) in the liquid remains less than 1000 ppm. Preferably, this content is maintained below 500 ppm, in particular in the range from 200 to 500 ppm. However, it is also equally possible to choose to maintain this content at a very low value, in particular considerably less than 200 ppm. In a specific embodiment, the hydrogenation reaction can advantageously be carried out in a chamber equipped with means for measuring the content of compound of formula (II) in the reaction liquid, the means for introduction of the compound of formula (II) optionally being subject to these measuring means.

Advantageously, the compound of formula (II) is gradually introduced into a liquid hydrogenation medium with agitation, so as to avoid excessively high concentrations, that is to say local concentrations greater than the maximum desired concentration.

Preferably, the liquid medium in which the hydrogenation of the compound of formula (II) is carried out is a solvent liquid both for the compound of formula (II) and for the various reaction products.

Indeed, the process according to the invention is particularly efficient when the reaction takes place in solution in a homogeneous liquid medium, that is to say in the presence of a single liquid phase. This homogeneous liquid medium or single-phase medium may, however, comprise suspended solid particles introduced as such into the medium, namely catalyst particles.

However, the reaction can also be carried out in heterogeneous medium, that is to say if the reactants are insoluble or partially soluble in the medium; the appropriate reaction conditions will be given in detail subsequently.

The solvent is preferably a polar solvent, which may be protic or aprotic. The relative dielectric constant $\epsilon$ of the said solvent is advantageously at least equal to 5, preferably less than or equal to 50. Advantageously, the solvent exhibits an acceptor number A of at least 8, preferably greater than or equal to 9. Reference will be made, for the definition of the acceptor number A, to the work by C. Reichardt, Solvents and Solvent Effects in Organic Chemistry, 2nd Edition, VCH (FRG), 1990, pp. 23–24. Solvents for which the donor number D, expressed by the variation in enthalpy ($\Delta H$ in kcal/mol) of the combination of the said solvent with antimony pentachloride, is from 10 to 30 are also advantageous. Use may in particular be made of methanol or ethyl acetate. The solvent can advantageously be chosen from water-miscible solvents.

When the reaction is carried out in alcoholic medium, it is preferable, to avoid side reactions due to the solvent, to limit the pH of the medium to a value less than or equal to 13.

Solvents containing sulphur capable of being reduced under the conditions of the hydrogenation, for example DMSO, are to be avoided because they result in undesired by-products which can, in particular, render the catalyst inactive. A sulphur-containing solvent, such as sulpholane, is, however, acceptable because it is very difficult to reduce.

Generally, it can be advantageous to carry out the reaction in a solvent with a boiling point sufficiently distant from that of the product to facilitate isolation of the reaction product by distillation.

The catalyst can be selected from any known hydrogenation catalyst, in particular metals such as nickel or palladium or metals from the platinum group, optionally on an inorganic or organic support, such as carbon black and/or active charcoal. Palladium proves to be very appropriate when the reaction is carried out in heterogeneous medium and the reaction is possible when operating at a temperature of at least approximately 100° C. and up to approximately 150° C. The positional zeros are not regarded as significant figures in the present description, unless otherwise specified.

The process of the invention can be applied to the preparation of fluoroanilines by hydrogenation of fluoronitrobenzenes, that is to say compounds of formula (II) where q has a value of 0.

In this case, the choice of the catalyst is less crucial and it is in particular possible to choose palladium-on-charcoal.

When the compound of formula (II) does not carry a hydrogenolysable substituent, that is to say if q=0, the catalytic hydrogenation only results in the reduction reaction of $NO_2$ to $NH_2$. The reaction temperature conditions can be from 0° to 150° C., preferably from 30° to 130° C.

The process of the invention can also be applied to the preparation of fluoroanilines by catalytic hydrogenation of chlorofluoronitrobenzenes, that is to say of compounds of formula (II) where p is zero and X represents Cl, very particularly to the preparation of difluoroanilines by catalytic hydrogenation of compounds of the type indicated where q has a value of 1 (chlorodifluoronitrobenzenes) or where q has a value of 2 (dichlorodifluoronitrobenzenes) or alternatively of 3 (trichlorodifluoronitrobenzenes). In this specific case, the process of the invention then results in the reduction of the nitro group to an amino group and the hydrogenolysis of the chlorine atom or atoms.

The reduction of the nitro group to an amino group, which results in the transitory or actual presence of the corresponding fluorinated and halogenated aminated benzene compound, and the hydrogenolysis of the X group or groups can take place simultaneously or, preferably, successively. The hydrogenolysis can take place on the aminated compound, as intermediate or transitional intermediate compound, or else simultaneously with the reduction of the nitrated compound.

Preferably, when q is not zero and X is a halogen atom other than fluorine, in particular a chlorine atom, the hydrogenation conditions are adapted in order to form in a stage a), a compound of formula (III)

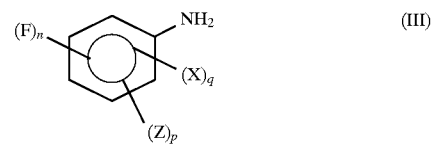

from the compound of formula (II) by catalytic reduction, then in a stage b), to form the compound of formula (I) from the compound of formula (III) by hydrogenolysis.

The conditions of the hydrogenation can be such that the same catalyst results in the reactions of the stage (a) and of the stage (b). Such a catalyst can comprise palladium-on-charcoal.

In this case, catalytic hydrogenation conditions which result in the reactions of the stages (a) and (b) simultaneously comprise a temperature of 50° to 130° C. The hydrogen pressure is advantageously from $10^5$ to $5 \times 10^6$ Pa in this case.

Hydrogenation conditions which result in first the conversion of substantially all the compound of formula (II) to a compound of formula (III) according to the stage (a), catalysed by palladium-on-charcoal, comprise a temperature of 0° to 70° C., in particular less than 60° C., preferably less than or equal to 50° C. The hydrogen partial pressure is preferably from $10^5$ to $2 \times 10^6$ Pa. Beyond 70° C., palladium-on-charcoal efficiently catalyses the reaction of the stage (b).

The stage (b) can then be carried out with a temperature greater than 80° C., in particular greater than 100° C., especially at 120° C. The hydrogen partial pressure is advantageously from $1.5 \times 10^6$ to $5 \times 10^6$ Pa during this stage.

The hydrogenation conditions can also be such that one catalyst is used for the stage (a) and another catalyst, distinct from the above, is used for the stage (b).

The hydrogenation catalyst can be selected in order selectively to obtain, at first, the compound of formula (III), which can be isolated. In this respect, preference is given to nickel, in particular Raney nickel, or a metal catalyst poisoned in a way known in the hydrogenation technique, for example poisoned Raney nickel. Mention may be made of the metal catalysts poisoned with sulphur as described in FR-A-2,664,590 and FR-A-2,649,979 and the metal catalysts poisoned with an iodide as described in FR-A-2,649,978. Preference is given to slightly poisoned catalysts, that is to say where the amount of poison is insufficient to render the catalyst completely inactive. The reaction is then preferably carried out at a temperature of less than 80° C., preferably of less than 70° C. The hydrogen partial pressure is preferably from $10^5$ to $2 \times 10^6$ Pa.

The reaction of the stage (b) can then take place subsequently by using another catalyst which does not form part of the group mentioned above and which is active in catalysing the said hydrogenolysis. Palladium-on-charcoal especially can in particular be used. The reaction is then preferably carried out at a temperature greater than 80° C., in particular greater than 100° C., especially greater than 120° C. The hydrogen partial pressure is preferably from $1.5 \times 10^6$ to $5 \times 10^6$ Pa in this stage.

In the case where it is desired to separate the compound of formula (III), that is to say reduced simply by the reaction of the stage (a), it is particularly advantageous to carry out the reaction in a solvent with a relatively high boiling point, in order to be able carefully to separate this intermediate product by distillation, optionally as it is synthesized, before the end of the stage (a).

Use may be made, as hydrogenation gas, of pure hydrogen or alternatively of a mixture of hydrogen and an inert gas, in particular nitrogen.

Under the temperature and pressure conditions indicated above, the reduction reaction of the nitro group to an amino group (stage (a)) is complete if the amount of hydrogen is unlimited.

The hydrogenolysis reaction of the X groups can be limited by the use of a selective catalyst, such as partially poisoned Raney nickel, or by the use of inadequate temperature and/or pressure conditions.

When X represents a halogen atom, the reaction of the stage (b) releases the halogen atom or atoms in the form of hydrohalic acid.

It is then advantageous to carry out the reaction in the presence of a base in order to neutralize the acid released. Generally, the pH should preferably be maintained at a value such that the bulk of the aniline formed, that is to say at least 80%, advantageously at least 90%, remains in the free form in the reaction medium.

The base added is preferably an alkaline base, in particular sodium hydroxide, which can be introduced into the medium in the form of an aqueous solution.

It is also possible to use alkaline-earth metal oxides, such as in particular MgO and CaO. These compounds are, however, difficult to dissolve in water or at least have very slow dissolution kinetics, so that their use can introduce a large amount of solids into the hydrogenation medium and thus cannot make it possible to achieve results which are as good as those obtained under the conditions suited to a homogeneous solution (leaving aside the solid catalyst). As was said above, it is, however, possible to carry out the reaction without problems in heterogeneous medium under appropriate conditions.

As an alternative form, it is also possible to use a basic ion-exchange resin as acidity-absorbing agent.

When the reaction is carried out in alcoholic medium, it is preferable, in order to avoid side reactions of substitution of the aromatic ring by species arising from the solvent, for the base used to be relatively weak, in particular for its pKa to be at least equal to that of the $Mg^{2+}$ ion and less than 13; or alternatively to adjust the pH by gradually adding the base so as to prevent the pH from exceeding 13. It is also possible to adjust the pH by using a buffer.

In the case where a basic aqueous solution is used, it is preferable to choose a water-miscible solvent for constituting the hydrogenation medium, so that hydrogenation takes place in homogeneous solution.

During the reaction, it is preferable for the amount of reactants present to be such that the concentration of the products (such as the nitrogenous base, or its hydrohalide, or the salts resulting from the reaction of the hydrohalic acid released with the base introduced) remains less than the solubility limit of each of these products in the reaction medium. Preferably, the precipitation of solid matter in the reaction medium is avoided by maintaining the concentrations of the species in solution at a value of less than 90%, more particularly at a value of less than 80%, of their solubility limit.

In this respect, the pH modification implied by the addition of base to the reaction medium can advantageously be taken advantage of in modifying the said solubility limits and in continuing to carry out the reaction in homogeneous solution.

However, it is not essential to carry out the reaction in homogeneous medium. The reaction is possible in heterogeneous medium by carrying out the reaction, in particular in the stage b), at a temperature of at least approximately 100° C. and up to approximately 150° C. (the positional zeros not being regarded as significant figures). Use will preferably be made of a palladium catalyst.

Use may be made of any known base in a variable amount but, when this base is provided in the form of a salt of low solubility, such as sodium hydroxide or potassium hydroxide, it is preferable for the concentration to be less than or equal to 1 mol/l, in particular less than or equal to 0.5 mol/l.

The base is advantageously introduced into the reaction medium in proportion as hydrohalic acid is released during the reaction.

As an alternative form, it is possible to carry out the reaction in the presence of base only from the end of the gradual introduction of compound of formula (II), optionally while raising the temperature of the reaction medium. In this case, it is also possible to introduce the base in proportion as hydrohalic acid is released.

When a selective catalyst is used with the aim of only, at first, carrying out the reaction of the stage (a), it is preferable for the reaction not to be carried out in the presence of a base, in order to limit the risks of side reactions.

On conclusion of the gradual introduction of the compound of formula (II), the latter has been completely reduced to an amine and the reaction medium can comprise solely the compound of formula (III) or alternatively a mixture of compound of formula (III) and of compound of formula (II), depending on the reaction conditions.

If the reaction mixture at the end of addition contains compound of formula (III), the hydrogenation operation can be continued in order to achieve the compound of formula (I) with a quantitative yield.

In this stage, the catalytic hydrogenation can be continued directly on the reaction mixture. If the reaction has until now been carried out with a selective catalyst which does not make possible the reaction (b), another catalyst, this time active with respect to this reaction, should be introduced into the hydrogenation medium.

As an alternative form, it is also possible to separate the reaction product of the hydrogenation, in the form of the compounds of formula (I) and of formula (III) or in the form of their mixture.

The compound of formula (III) can then be subjected, alone or as a mixture with the compound of formula (I), to a further catalytic hydrogenation operation in a hydrogenation chamber containing a liquid medium which is a solvent for the fluorinated anilines in the presence of a hydrogenation catalyst and of a base. The reaction medium can be identical to or different from the reaction medium for the first hydrogenation, the advantageous alternative forms set out above preferably being observed (in particular in choosing a polar solvent, advantageously one which is water-miscible, and the like).

All the alternative forms set out above make it possible to achieve a quantitative conversion of the starting benzene compound with a virtually quantitative yield of fluorinated aniline.

The hydrogenation is preferably carried out in a single medium by linking together the reactions (a) and (b) in order in fine to obtain the compound of formula (I). The reaction is preferably carried out in the presence of palladium-on-charcoal as catalyst. The catalyst can advantageously contain 5 to 15% of palladium. The temperature is preferably maintained at less than 70° C. during the gradual introduction of the compound of formula (II) and it is then brought to a value greater than 80° C., preferably greater than 100°–120° C., to bring the reaction to completion.

The fluorinated aniline obtained can be separated from the reaction medium at the end of hydrogenation, in particular by distillation.

At the end of the hydrogenation reaction, it is possible to achieve a concentration of amine which can range up to 50% by weight of the reaction medium. Concentrations greater than 20% by weight are very easily achieved.

This possibility of obtaining final products which are highly concentrated in the reaction medium makes it possible to improve the productivity of the equipment, which represents an additional advantage of the process of the invention, in addition to its high yield.

The process according to the present invention can be applied highly advantageously to the preparation of 2,4-difluoroaniline of formula (Ia)

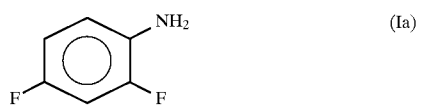

by catalytic hydrogenation of compounds of formula (IIa)

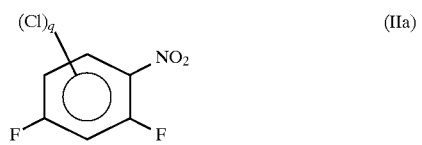

in which q is an integer from 0 to 2, the optional chlorine atom or atoms being in the meta position with respect to the nitro group.

As the hydrogenation of these compounds results in the same final product, the reaction can be carried out with a mixture of these compounds.

Scheme 1 provides a multi-stage synthesis of 2,4-difluoroaniline using this hydrogenation and starting from very simple precursors.

SCHEME I

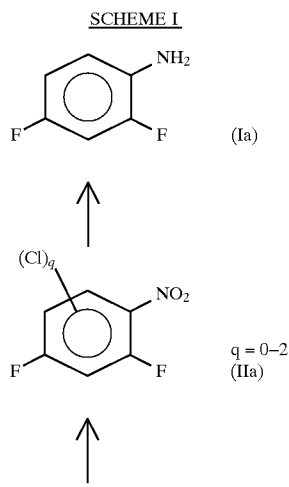

-continued
SCHEME I

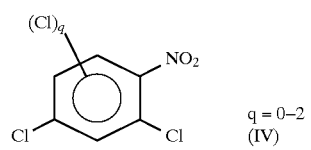

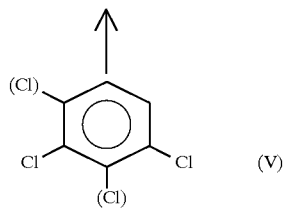

A compound or a mixture of compounds of formula (IIa)

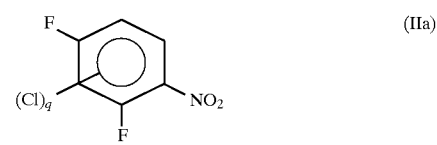

where q has a value from 0 to 2, selected from 2,4-difluoronitrobenzene and its derivatives which are chlorinated in the 3- or 5-position or in the 3- and 5-positions, can be obtained by reaction of a compound or of a mixture of compounds of formula (IV)

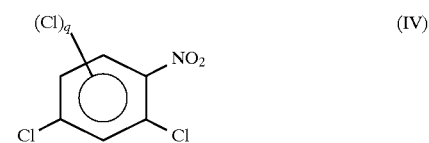

selected respectively from 2,4-dichloronitrobenzene and its derivatives which are chlorinated in the 3- or 5-position or in the 3- and 5-positions, with a source of fluorides.

It is the chlorine atoms in the ortho and para positions which are substituted by fluorine atoms. The poorer the ring, in particular with respect to the other Cl substituents, the easier the exchange.

Use is conventionally made, as fluoride source, of an alkali metal fluoride, in particular a potassium or caesium fluoride, or a quaternary ammonium fluoride, in a slight excess calculated with respect to the two ortho and para chlorine atoms to be substituted by fluorine.

The reaction preferably takes place in a dry polar aprotic solvent known to the person skilled in the art exhibiting in particular the dielectric constant $\epsilon$ and donor number D characteristics indicated above.

The compound or the mixture of compounds of formula (IV) is advantageously obtained by reaction of a compound or of a mixture of compounds of formula (V)

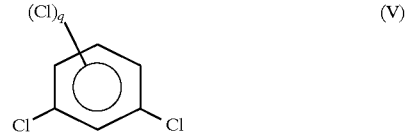

selected respectively from 1,3-dichlorobenzene and its derivatives which are chlorinated in the 2- or 4-position or in the 2- and 4-positions, with a reagent for the nitration of aromatic compounds, in particular with nitric acid.

The nitro functional group is introduced into the 6-position of 1,2,3-trichlorobenzene to the extent of 96% and into the 5-position of 1,2,4-trichlorobenzene to the extent of 90%.

Whatever the chlorinated benzene compound of formula (V) used at the beginning of the reaction sequence, the final product is 2,4-difluoroaniline of formula (Ia). It is thus possible to carry out the reaction without any danger with starting mixtures containing various chlorinated benzene compounds.

Likewise, the process according to the present invention can be applied to the preparation of 3,5-difluoroaniline of formula (Ib)

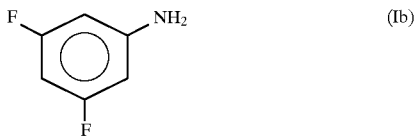

(Ib)

by catalytic hydrogenation of a compound or of a mixture of compounds of compounds [sic] of formula (IIb)

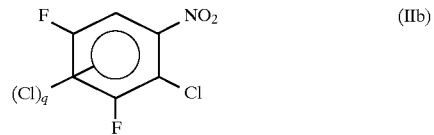

(IIb)

where q has a value from 0 to 2, selected from 2-chloro-3,5-difluoronitrobenzene and its derivatives which are chlorinated in the 4- or 6-position or in the 4- and 6-positions.

Scheme 2 provides two routes for the multi-stage synthesis of 3,5-difluoroaniline using this hydrogenation and starting from very simple precursors.

SCHEME 2

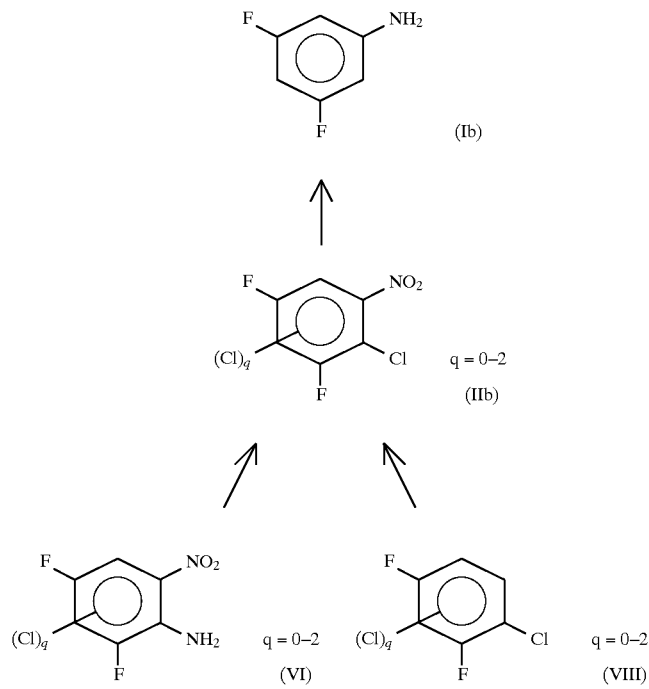

-continued
SCHEME 2

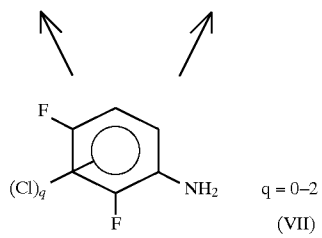
(VII)

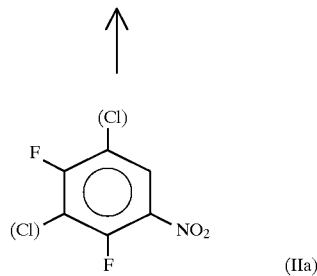
(IIa)

A compound or a mixture of compounds of formula (IIb)

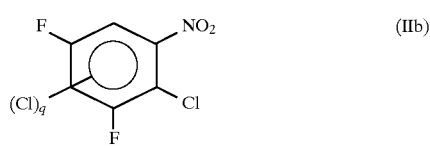
(IIb)

where q has a value from 0 to 2, selected from 2-chloro-3,5-difluoronitrobenzene and its derivatives which are chlorinated in the 4- or 6-position or in the 4- and 6-positions, can be obtained by reaction of a compound or of a mixture of compounds of formula (VI)

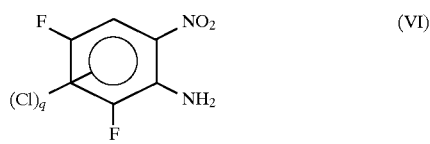
(VI)

selected respectively from 2-amino-3,5-difluoronitrobenzene and its derivatives which are chlorinated in the 4- or 6-position or in the 4- and 6-positions, with cuprous chloride in the presence of a source of nitrite ions, in particular of nitrous acid or of sodium nitrite in acid medium.

This reaction, known under the name of Sandmeyer reaction, results in a diazotization on the nitrogen atom of the amine functional group, the azo group subsequently being substituted by a chlorine atom.

It turned out that this reaction is particularly efficient with the compounds mentioned above and the present Inventors have been able to observe very high reaction yields, considerably greater than 90%.

The compound or the mixture of compounds of formula (VI) is obtained by reaction of a compound or of a mixture of compounds of formula (VII)

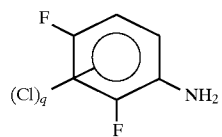
(VII)

selected respectively from 2,4-difluoroaniline and its derivatives which are chlorinated in the 3- or 5-position or in the 3- and 5-positions, with a reagent for the nitration of aromatic compounds, in particular with nitric acid.

One of the best media for carrying out this nitration reaction is a medium which contains nitric acid, sulphuric acid and a carboxylic acid.

Advantageously, the reaction mixture can also contain a significant proportion of water which can be introduced as such or via a solution of one of the abovementioned inorganic acids.

Advantageously, the water content of the reaction medium, not, of course, taking into account the starting material, is between 1/10th and one times the amount of pure nitric acid used.

The amount of water introduced by using a 65% nitric acid leads to satisfactory results.

Preferably, before the nitration reaction, the amino group of the aniline can be deactivated by acylation. The acyl group can be introduced conventionally by reaction of the aniline with an acid anhydride or acid halide or with compounds deriving from carbonic acid by monoamidation.

However, it is preferable for the anilides to remain stable under the conditions of the nitration reaction.

The reaction of cleaving of the anilide to restore the aniline can be carried out in the same reaction system as that of the nitration. To do this, it is sufficient to heat the reaction mixture resulting from the nitration at a temperature at least equal to 50° C., preferably at least equal to 80° C., optionally after addition of a certain amount of water.

The product from the nitration reaction, with or without involving the anilide, results in a final product in the form of a nitroaniline salt. This salt can be used in the Sandmeyer reaction in the same way as the nitroaniline itself.

In an alternative form, the compound or the mixture of compounds of formula (IIb) can advantageously be obtained, by reversing the order of the nitration and Sandmeyer reactions, from compound(s) of formula (VII).

Thus, a compound or a mixture of compounds of formula (IIb)

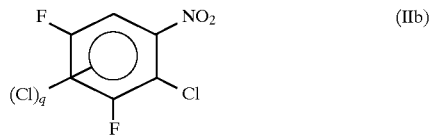

where q has the value from 0 to 2, selected from 2-chloro-3,5-difluoronitrobenzene and its derivatives which are chlorinated in the 4- or 6-position or in the 4- and 6-positions, can be obtained by reaction of a compound or of a mixture of compounds of formula (VIII)

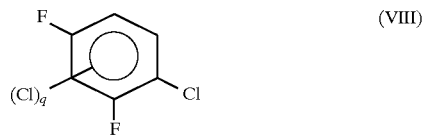

selected respectively from 1-chloro-2,4-difluorobenzene and its derivatives which are chlorinated in a 3- or 5-position or in the 3- and 5-positions, with a reagent for the nitration of aromatic compounds, in particular with nitric acid.

Nitration meta to the two fluorine atoms is carried out easily and regioselectively.

The compound or the mixture of compounds of formula (VIII) is preferably obtained by subjecting a compound or a mixture of compounds of formula (VII)

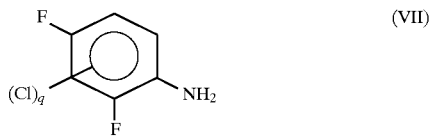

selected respectively from 2,4-difluoroaniline and its derivatives which are chlorinated in the 3- or 5-position or in the 3- and 5-positions, to the Sandmeyer reaction.

This alternative form is very advantageous with respect to the reaction sequence explained above, since it makes it possible to avoid the stage of protection of the amine in the presence of the nitro group by converting to the anilide, which involves expensive reagents and which implies the need to treat effluents produced during the application of the Sandmeyer reaction to the chlorofluoronitroaniline protected in the anilide form.

The compound or the mixture of compounds of formula (VII) can advantageously be obtained by hydrogenation of a compound or of a mixture of compounds of formula (IIa)

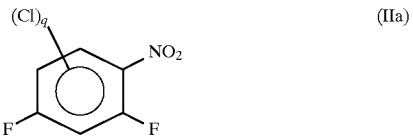

where q has a value from 0 to 2, selected from 2,4-difluoronitrobenzene and its derivatives which are chlorinated in the 3- or 5-position or in the 3- and 5-positions, in particular according to a catalytic hydrogenation process according to the invention as described above.

Any known method for the reduction of a nitro group to an amino group can be used, provided that this method does not affect the halogen, and especially fluorine, substituents.

In this respect, mention may be made of a reduction by catalytic hydrogenation at room temperature, it being possible for the catalyst to be in particular palladium or Raney nickel.

However, it is preferable to apply the reduction conditions according to the present invention, in particular by employing a slightly poisoned catalyst which is selective for the reduction and which does not make dechlorination possible.

It is thus possible to prepare, with a good yield, 2,4- and 3,5-difluoroaniline from simple precursors, namely 1,3-dichlorobenzene, 1,2,3- and 1,2,4-trichlorobenzene, and 1,2,3,4-tetrachlorobenzene, or mixtures of these precursors, since all result in the same final major product. The sequence of reactions can be carried out by isolating each intermediate product at each stage. It is also possible to use, in a stage, the crude reaction mixture resulting from the preceding stage. To do this, a universal solvent system will be used. Sulpholane is fairly well suited. However, care will be taken that the reaction mixtures do not contain by-products, in particular sulphur-containing products, which are capable of constituting or of generating poisons with respect to the catalyst or catalysts of the hydrogenation reactions.

Thus, a process for the preparation of 2,4-difluoroaniline according to the invention can comprise:
(i) the reaction of 1,2,3-trichlorobenzene with a nitration reagent, in particular nitric acid, to give 2,3,4-trichloronitrobenzene (A),
(ii) bringing (A) and potassium fluoride together in order to form 3-chloro-2,4-difluoronitrobenzene (B),
(iii) the catalytic hydrogenation of (B) according to a process as described above.

This process also makes it possible to synthesize 2,4-difluoroaniline by using 1,2,4-trichlorobenzene or 1,2,3,4-trichlorobenzene, or even a mixture of at least two products selected from 1,2,3-trichlorobenzene, 1,2,4-trichlorobenzene and 1,2,3,4-tetrachlorobenzene, in the stage (i). The intermediate products or mixtures of intermediate products react with the same reagents in the stages (ii) and (iii), to result, on conclusion of the stage (iii), in mainly 2,4-difluoroaniline. The possible by-product isomers, 2,6-difluoroaniline or 3,5-difluoroaniline, can easily be separated by distillation.

Likewise, a process for the preparation of 3,5-difluoroaniline according to the invention can comprise the series of following stages or alternatively another sequence involving one or a number of these stages in order to prepare 2,4-dichloro-3,5-difluoronitrobenzene:
(i) the reaction of 1,2,3-trichlorobenzene with a nitration reagent, in particular nitric acid, to give 2,3,4-trichloronitrobenzene (A),
(ii) bringing (A) and potassium fluoride together in order to form 3-chloro-2,4-difluoronitrobenzene (B),
(iii) the catalytic hydrogenation of (B) under conditions which do not affect the chlorine atom, in particular according to a process as described above, in order to result in 3-chloro-2,4-difluoroaniline (C),
(iv) the reaction of (C) with a nitration reagent, resulting in 3-chloro-2,4-difluoro-6-nitroaniline (D),
(v) bringing (D), cuprous chloride and a source of nitrite ions, in particular nitrous acid, together in order to form 2,4-dichloro-3,5-difluoronitrobenzene (E),
and finally
(vi) the catalytic hydrogenation of (E) according to a process as described above.

This process makes it possible to prepare 3,5-difluoroaniline by using 1,2,4-trichlorobenzene or 1,2,3,4-trichlorobenzene, or even a mixture of at least two products selected from 1,2,3-trichlorobenzene, 1,2,4-trichlorobenzene and 1,2,3,4-tetrachlorobenzene, in the stage (i). All the starting materials result mainly in 3,5-difluoroaniline on conclusion of the stage (vi). When a mixture of starting materials is used, this mixture results, whatever its proportions, in a final product mainly containing 3,5-difluoroaniline. The possible by-product isomers, 2,6-difluoroaniline or 2,4-difluoroaniline, can easily be separated by distillation.

This process results in 3,5-difluoroaniline with a high yield. In addition, with respect to the known processes, it has the advantage of not involving a chlorodenitration reaction which releases $NO_2Cl$ as by-product. This explosive by-product has, until now, limited the possibilities of industrial synthesis of 3,5-difluoroaniline. The process described above offers a sure and financially viable solution to the problem of the industrial synthesis of 3,5-difluoroaniline.

A process of the abovementioned type, which comprises the stages (i) and (ii), has the advantage of being able equally well to manufacture 2,4-difluoroaniline with the same industrial equipment, by simple modification of the conditions of the hydrogenation of the stage (iii). An industrialist who has available this multipurpose equipment can easily adapt his production according to demand.

Another process for the preparation of 3,5-difluoroaniline according to the invention can comprise:
(i) the reaction of 1,2,4-trichlorobenzene, optionally of its derivative which is chlorinated in the 3-position, with a nitration reagent, in particular nitric acid,
(ii) bringing the 2,4,5-trichloronitrobenzene, optionally chlorinated in the 3-position, thus obtained and potassium fluoride together,
(iii) the catalytic hydrogenation of the 5-chloro-2,4-difluoronitrobenzene, optionally chlorinated in the 3-position, thus obtained under conditions which do not affect the chlorine atom, in particular according to a process as described above,
(iv) the reaction of the 5-chloro-2,4-difluoroaniline, optionally chlorinated in the 3-position, thus obtained with cuprous chloride in the presence of a source of nitrite ions, in particular of nitrous acid,
(v) bringing the 1,3-dichloro-4,6-difluorobenzene, optionally chlorinated in the 5-position, thus obtained and a nitration reagent, in particular nitric acid, together and
(vi) the catalytic hydrogenation of the 2,6-dichloro-3,5-difluoronitrobenzene, optionally chlorinated in the 4-position, thus obtained according to a process as described above.

This process, which, surprisingly, only involves reactions of very high regioselectivity, makes it possible to arrive at 3,5-difluoroaniline with a very good yield and a production cost which are compatible with an industrial application. It is possible, in this case again, to use a mixture of starting materials in order to result in a final product in which the major component greatly predominates. By virtue of these processes, it is thus possible to enhance the value of the mixtures of isomers of chlorinated benzene compounds resulting from successive chlorinations of dichlorobenzene. Thus, the monochlorination of ortho-, meta- or para-dichlorobenzene, which results in a mixture of 1,2,3- and 1,2,4-trichlorobenzene which can be further substituted by a chlorine atom to give 1,2,3,4-tetrachlorobenzene.

The present invention will now be illustrated by means of the following examples.

EXAMPLES

Examples 1 to 4: Reduction of 3-chloro-2,4-difluoronitrobenzene to 3-chloro-2,4-difluoroaniline.

All the tests were carried out from starting materials with a purity greater than 95%.

Example 1

Reduction of 3-chloro-2,4-difluoronitrobenzene to 3-chloro-2,4-difluoroaniline.

0.18 g of Raney nickel are placed in 100 ml of methanol in a 300 ml stainless steel reactor stirred at 1000 revolutions/minute which is equipped with a pump for injection under pressure and with a capacity (supply and pressure-reducing gauge) which makes it possible to control the pressure in the reactor and to measure the amount of hydrogen consumed.

The reactor is purged three times with nitrogen and then three times with hydrogen.

The temperature of the reactor is brought to 50° C. and a hydrogen pressure of $1.5 \times 10^6$ Pa is introduced. When these conditions are established, 50 ml of a solution of 18 g (0.093 mol) of 3-chloro-2,4-fluoronitrobenzene in methanol is injected at the rate of 28 ml/h.

The temperature and pressure conditions are kept constant throughout the injection, the concentration of 3-chloro-2,4-difluoronitrobenzene being maintained, by the injection flow rate, at a value of less than 500 ppm.

After the end of introduction of the 3-chloro-2,4-difluoronitrobenzene, the hydrogenation conditions are maintained for one hour without observing additional hydrogen uptake, indicating that the reaction is complete.

By simple distillation of the solvent, 15.3 g of a very light-coloured product are separated, which product contains 99.5% of 3-chloro-2,4,-difluoroaniline and contains only 0.02% of 2,4-difluoroaniline.

The degree of conversion of the 3-chloro-2,4,-difluoronitrobenzene is 100% and the 3-chloro-2,4-difluoroaniline yield is 99.6%.

The rate of the reaction (disappearance of the starting material) was approximately 0.2 $mol.h^{-1}.g^{-1}$ of catalyst.

Example 2

The reaction is carried out in a 300 ml reactor stirred with a propeller which provides excellent gas/liquid transfer, so that the medium is always saturated with hydrogen under the conditions of the reaction.

120 ml of ethyl acetate and 0.18 g of Raney nickel, washed beforehand with ethanol and ethyl acetate, are charged to the reactor. After removing the air with nitrogen and then the nitrogen with hydrogen, the reactor is pressurized under $1.5 \times 10^6$ Pa absolute with hydrogen at a temperature of 50° C. A solution of 0.093 mol of 3-chloro-2,4-difluoronitrobenzene dissolved in 80 ml of ethyl acetate is injected over 225 min.

The hydrogen consumption invariably corresponds to the stoichiometry of 3 mol per mole of nitrated derivative.

It is confirmed, by appropriate analytical means (continuous potential measurement and monitoring by gas phase chromatography GPC), that the concentration of nitrated derivative remains less than or equal to 500 ppm.

After halting the injection of nitrated derivative, the temperature and pressure conditions are maintained for a further 15 min without hydrogen consumption being observed.

The 3-chloro-2,4-difluoroaniline yield (quantitatively determined by GPC) is 99.6%. The formation of 0.4% of 2,4-difluoroaniline is also observed, this product resulting from the hydrodechlorination of the 3-chloro-2,4-difluoroaniline produced.

Example 3

The reaction is carried out as in Example 2 but in a water/methanol (10/90 by volume) mixture as solvent and with palladium-on-charcoal containing 10% of Pd as catalyst.

100 ml of the water/methanol mixture and 200 mg of catalyst are placed in the reactor.

The reactor is pressurized to $4 \times 10^5$ Pa with hydrogen and heated to 60° C. The 3-chloro-2,4-difluoronitrobenzene (0.18 mol) is dissolved in 70 ml of methanol and injected into the reactor over 150 min.

The concentration of nitrated derivative is less than 500 ppm throughout the duration of the hydrogenation.

The 3-chloro-2,4-difluoroaniline yield (quantitatively determined by GPC) is 88.5%. 10.2% of 2,4-difluoroaniline, resulting from the hydrodechlorination of the 3-chloro-2,4-difluoroaniline produced, are also present.

This example shows that palladium-on-charcoal is a catalyst capable of catalysing both the reduction of the nitro group and the substitution of the chlorine atoms by hydrogen.

Analysis of the fluorides in the liquid medium and in the catalyst shows that hydrodefluorination is less than 0.1% with respect to the nitrated derivative used.

Example 4

The reaction is carried out as in Example 2 with different charges and conditions.

180 ml of a methanol/water mixture (in a 66/34 ratio by volume) and 300 mg of Raney nickel are placed in the reactor. The reactor is pressurized to $2 \times 10^6$ Pa with hydrogen and heated to 60° C. The pressure is then kept constant at $2.2 \times 10^6$ Pa.

A solution of 0.155 mol of 3-chloro-2,4-difluoronitrobenzene in 70 ml of methanol is injected over 270 min.

The 3-chloro-2,4-difluoroaniline yield is 87% and the 2,4-difluoroaniline yield is 13%.

Comparative Examples 1 to 3

The hydrogenation of 3-chloro-2,4-difluoronitrobenzene is carried out while placing all the nitrated benzene compound in the reactor at the beginning of the reaction.

Comparative Example 1

10g of 3-chloro-2,4-difluoronitrobenzene (0.049 mol) are placed, with 13 ml of chlorobenzene, 0.8 ml of water and 0.08 g of platinum-on-charcoal containing 5% of platinum, in 38 ml of methanol in a stainless steel autoclave agitated with a shaking motion which is equipped with a capacity which makes it possible to control the pressure in the autoclave and to measure the amount of hydrogen consumed. The chlorobenzene is used to prevent any untimely dehalogenation.

The autoclave is purged three times with nitrogen and then three times with hydrogen.

The temperature of the autoclave is brought to 35° C. and a hydrogen pressure of $4.2 \times 10^6$ Pa is introduced. The pressure is maintained at this value by continuous introduction of hydrogen, whereas the temperature rises to 50° C. because of the exothermicity of the reaction. The reaction is complete in 45 minutes.

After this period, it is verified that the degree of conversion of the starting 3-chloro-2,4-difluoronitrobenzene is 100%. The degree of formation of 3-chloro-2,4-difluoroaniline is likewise measured and has a value of 81%, the remainder of the conversion product being composed of various products, including halogenated nitrated benzene compounds with azo or azoxy functional groups, optionally having lost chlorine and fluorine. The 3-chloro-2,4-difluoroaniline can be isolated by distillation and then subjected to a salification in the hydrochloride form and further distillation. These purification operations, however, cause the yield to fall to approximately 50%.

The rate of the reaction was 0.83 mol.h$^{-1}$.g$^{-1}$ of catalyst.

Comparative Example 2

3.7 g of 3-chloro-2,4-difluoronitrobenzene (0.018 mol) are placed, with 30 mg of palladium-on-charcoal containing 10% of Pd, in 100 ml of methanol containing 4% of water in a stainless steel autoclave agitated with a shaking motion which is equipped with a capacity which makes it possible to control the pressure in the autoclave and to measure the amount of hydrogen consumed.

The temperature of the autoclave is brought to 35° C. and a hydrogen pressure of $1 \times 10^5$ Pa is introduced. The pressure and the temperature are maintained for 400 minutes.

After this heating period, it is verified that the degree of conversion of the starting 3-chloro-2,4-difluoronitrobenzene is 100%. The degree of formation of 3-chloro-2,4-difluoroaniline is likewise measured and has a value of 84%, the remainder of the conversion product being composed of the same products as in Comparative Example 1.

The rate of the reaction was in the region of 0.1 mol.h$^{-1}$.g$^{-1}$ of catalyst.

Comparative Example 3

Comparative Example 2 is repeated with 90 mg of catalyst and 14.8 g of 3-chloro-2,4-difluoronitrobenzene.

The duration of the reaction is 400 min. The degree of conversion of the nitrated derivative is 100%. The 3-chloro-2,4-difluoroaniline yield is 57%. The remainder is still composed of the same by-products as in Comparative Examples 1 and 2.

Comparative Example 4 (with respect to Example 3)

In this comparative example, the hydrogenation is carried out while introducing the 3-chloro-2,4-difluoronitrobenzene gradually but without observing the condition according to which the 3-chloro-2,4-difluoronitrobenzene content in the reaction medium remains below 1000 ppm.

0.20 g of palladium-on-charcoal containing 10% of Pd is placed in 90 ml of methanol and 10 ml of water in a 300 ml stainless steel reactor stirred at 1000 revolutions/minute which is equipped with a pump for injection under pressure and with a capacity (supply and pressure-reducing gauge) which makes it possible to control the pressure in the reactor and to measure the amount of hydrogen consumed.

The reactor is purged three times with nitrogen and then three times with hydrogen.

The temperature of the reactor is brought to 60 ° C. and a hydrogen pressure of $3 \times 10^5$ Pa is introduced. When these conditions are established, 50 ml of a solution of 39 g (0.2 mol) of 3-chloro-2,4-difluoronitrobenzene in methanol are injected at the rate of 28 ml/h.

The temperature and pressure conditions are kept constant throughout the injection.

After the end of the introduction of the 3-chloro-2,4-difluoronitrobenzene, the hydrogenation conditions are maintained for one hour without observing additional hydrogen uptake, thus indicating that the reaction is complete.

A light-coloured product is separated by simple distillation of the solvent.

The total yield for formation of anilines is measured and has a value of 88%.

The degree of conversion of the 3-chloro-2,4-difluoronitrobenzene is still 100%.

Example 1, when compared with Comparative Examples 1, 2 and 3, clearly demonstrates the remarkable improvement in the yield of the reducing hydrogenation reaction by virtue of the gradual injection of the starting material while maintaining a concentration of nitrated compound of less than 1000 PPm.

Examples 5 to 8

Hydrodehalogenation of 3-chloro-2,4-difluoroaniline to form 2,4-difluoroaniline (hydrodechlorination).

Example 5

1.64 g of 3-chloro-2,4-difluoroaniline of Example 1, 0.05 g of palladium-on-charcoal containing 10% of Pd in 22 ml of methanol, with 11 ml of a 1 mol/l sodium hydroxide solution (0.011 mol), are charged to a 125 ml agitated bomb (autoclave), sold by the Company Prolabo, which is agitated with a shaking motion.

The closed autoclave is purged three times with nitrogen at a pressure of $3 \times 10^5$ Pa and then three times with hydrogen at a pressure of $3 \times 10^5$ Pa.

The pressure in the autoclave is brought to $2 \times 10^6$ Pa of hydrogen and the temperature is raised to 90° C. over 25 minutes. These conditions are maintained for 3 hours.

At the end of this time, the degree of conversion of the 3-chloro-2,4-difluoroaniline is determined by gas phase chromatography at 98%.

The 2,4-difluoroaniline yield is 97.5%.

The rate of the reaction was 0.065 $mol.h^{-1}.g^{-1}$ of catalyst.

The overall yield of Examples 1 and 2 for the preparation of 2,4-difluoroaniline by catalytic hydrogenation from 3-chloro-2,4-difluoronitrobenzene is 97.1%.

Example 6

44 ml of methanol, 22 ml of water, 0.1 g of Raney nickel, 0.022 mol of sodium hydroxide and 0.02 mol of 3-chloro-2,4-difluoroaniline are charged to a reactor stirred with a propeller providing, under the conditions of the reaction, a hydrogen gas/liquid transfer such that the medium is always saturated with hydrogen.

Heating is carried out to 90° C. under hydrogen pressure which is kept constant at $7.5 \times 10^5$ Pa absolute at 90° C. The reaction is complete after 4 hours.

The final degree of conversion of the 3-chloro-2,4-difluoroaniline is 75.5%. The 2,4-difluoroaniline yield is 80% with respect to the conversion product and there is 20% of aniline.

Raney nickel has little effectiveness in carrying out the hydrodechlorination reaction and, moreover, to a significant extent catalyses the hydrodefluorination of the 2,4-difluoroaniline under these conditions.

Example 7

88 ml of methanol, 44 ml of water, 0.2 g of palladium-on-charcoal containing 10% Pd and 0.04 mol of 3-chloro-2,4-difluoroaniline are charged to the same reactor as that of Example 6.

A hydrogen pressure is introduced in the reactor, which is heated to 90° C. The hydrogen pressure is kept constant at $1.9 \times 10^6$ Pa absolute at 90° C. During the reaction, sodium hydroxide is added in proportion as hydrochloric acid is given off until an amount is reached which is comparable with that used for a corresponding amount of chlorodifluoroaniline in Example 6.

After a period of 3 hours, the degree of conversion of the 3-chloro-2,4-difluoroaniline is 100% and the 2,4-difluoroaniline yield is 99%. The remainder of the conversion product (1%) is composed of 4-fluoroaniline and of traces of aniline.

Example 8

Example 7 is repeated at 125° C. under $2 \times 10^6$ Pa of hydrogen. After 2 hours, the 2,4-difluoroaniline yield is 99.2% and that of 4-fluoroaniline is 0.8%.

Example 9

Hydrogenation of 3-chloro-2,4-difluoronitrobenzene to 2,4-difluoroaniline in a single reactor linking together the reduction and then hydrodechlorination reactions.

160 ml of methanol and 30 ml of water, as well as 0.2 g of palladium-on-charcoal containing 10% Pd, are charged to the reactor described in Example 1. A solution of 0.207 mol of 3-chloro-2,4-difluoronitrobenzene in 100 ml of methanol is injected over 5 hours. The reactor is pressurized under $2 \times 10^6$ Pa, kept constant, and its temperature is 60° C. The hydrogenation being complete at the end of this period, 0.22 mol of sodium hydroxide is added in the form of a concentrated aqueous solution and heating is carried out at 120° C. while maintaining the pressure at $2 \times 10^6$ Pa of hydrogen.

After reacting for 5 hours, measurement by gas phase chromatography shows that the degree of conversion of the 3-chloro-2,4-difluoronitrobenzene used is 100% and the degree of 2,4-difluoroaniline is 95% with respect to the 3-chloro-2,4-difluoronitrobenzene used. The 2,4-difluoroaniline can easily be isolated from the reaction medium by distillation.

Example 10

Hydrodechlorination of 2,6-dichloro-3,5-difluoroaniline to 3,5-difluoroaniline in the presence of sodium hydroxide.

30 g of an approximately 30% by weight solution of 2,6-dichloro-3,5-difluoroaniline in a 13/1 by weight methanol/water mixture are charged to a 150 ml reactor. 0.25 g of palladium-on-charcoal catalyst containing 10% of Pd and 12 g of 30% sodium hydroxide solution are added. The reactor is purged under nitrogen and under hydrogen. The reactor is brought to 120° C. under $2 \times 10^6$ Pa of hydrogen. The reaction is complete after 2 hours: the degree of conversion is 100% and the 3,5-difluoroaniline conversion yield is 90%.

The remainder of the conversion product comprises fluoromethoxyaniline formed by nucleophilic aromatic substitution in the basic methanolic medium.

This side reaction can be eliminated by using a weaker base, as is shown in the following example.

Example 11

Hydrodechlorination of 2,6-dichloro-3,5-difluoroaniline to 3,5-difluoroaniline in the presence of magnesium oxide.

45 g of a 20% by weight solution of 2,6-dichloro-3,5-difluoroaniline in a 14/1 by weight methanol/water mixture are charged to a 150 ml reactor. 0.25 g of palladium-on-charcoal catalyst containing 10% Pd and 18 g of a 10% aqueous magnesium oxide suspension (MgO) are added. The reactor is purged with nitrogen and then with hydrogen and the reactor is then brought to 120° C. under $2 \times 10^6$ Pa with hydrogen. The reaction is halted after 6 hours: the degree of conversion is 97.2% and the 3,5-difluoroaniline conversion yield is 80.1%. The other conversion product is the still monochlorinated derivative (2-chloro-3,5-difluoroaniline, which can be converted to 3,5-difluoroaniline by continuing the hydrogenation. In this case, there is no nucleophilic aromatic substitution side reaction due to the solvent, by virtue of the low basicity of the magnesium oxide. The temperature conditions make it possible to carry out the reaction in the presence of a magnesium oxide suspension without any problem.

What is claimed is:

1. A process for the preparation of a compound of formula (I):

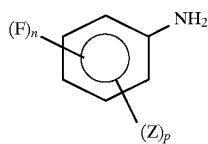

wherein n has a value from 1 to 5;
Z is a radical which is stable under catalytic hydrogenation conditions; and
p is less than 5−n;
comprising the step of subjecting a compound of formula (II):

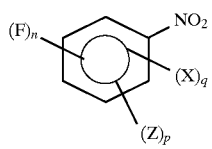

wherein n, Z and p have the above meanings;
X is a hydrogenolysable radical; and
q has a value from 0 to 5−(n+p);
to a catalytic hydrogenation in a liquid medium containing a catalyst, under hydrogen pressure in order to carry out a catalytic reduction reaction and, optionally, a hydrogenolysis reaction, wherein the compound of formula (II) is introduced gradually into the said liquid medium so that the content of compound of formula (II) in the liquid medium remains less than or equal to 1000 ppm by mass, in order selectively to form the compound of formula (I).

2. A process according to claim 1, wherein the compound of formula (II) is gradually introduced into the said liquid medium so that the content of compound of formula (II) in the liquid medium remains less than or equal to 500 ppm by mass.

3. A process according to claim 2, wherein the compound of formula (II) is gradually introduced into the said liquid medium so that the content of compound of formula (II) in the liquid medium is in the range from 200 to 500 ppm by mass.

4. A process according to claim 1, wherein X is a chlorine atom and q has a value from 1 to 5−(n+p), and the hydrogenation conditions are adapted in order to form in a stage a), a compound of formula (III):

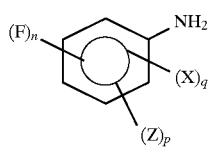

from the compound of formula (II) by catalytic reduction; and then in a stage b), to form the compound of formula (I) from the compound of formula (III) by hydrogenolysis.

5. A process according to claim 1, wherein the catalyst is the same throughout the hydrogenation and comprises palladium-on-charcoal.

6. A process according to claim 4, wherein the catalyst of the stage a) is a Raney nickel or poisoned metal catalysts and the catalyst of the stage b) is not a Raney nickel or poisoned metal catalysts.

7. A process according to claim 1, wherein the said liquid medium is a protic or aprotic polar solvent.

8. A process according to claim 1, wherein the reaction temperature is from 0° to 80° C. throughout the hydrogenation, if q=0, or during the stage (a), if q>0.

9. A process according to claim 1, wherein the hydrogen partial pressure during the hydrogenation is from $10^5$ to $5 \times 10^6$ Pa throughout the hydrogenation, if q=0, or during the stage (a), if q>0.

10. A process according to claim 5, wherein the said liquid medium further contains a base.

11. A process according to claim 5, wherein a base is introduced into the liquid medium in the stage (b).

12. A process according to claim 11, wherein the base is an alkaline base.

13. A process according to claim 11, wherein the said base is sodium hydroxide, present in the liquid medium at a concentration of less than or equal to 1 ml/l.

14. A process according to claim 5, wherein the reaction temperature in the stage (b) is from 80° to 150° C.

15. A process according to claim 5, wherein the hydrogen partial pressure in the stage (b) is from $1.5 \times 10^6$ to $5 \times 10^6$ Pa.

16. A process according to claim 1 for the preparation of 2,4-difluoroaniline of formula (Ia):

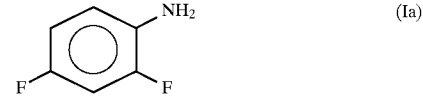

comprising the step of subjecting a compound or mixture of compounds of formula (IIa):

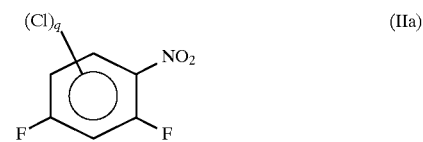

wherein q has a value from 0 to 2, selected from the group consisting of 2,4-difluoronitrobenzene, the derivatives of 2,4-difluoronitrobenzene chlorinated in the 3-position, the derivatives of 2,4-difluoronitrobenzene chlorinated in the 5-position, and the derivatives of 2,4-difluoronitrobenzene chlorinated in the 3- and 5-positions, to catalytic hydrogenation.

17. A process according to claim 16, wherein the compound or the mixture of compounds of formula (IIa) is obtained by reaction of a compound or of a mixture of compounds of formula (IV):

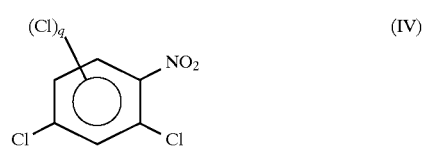

selected respectively from 2,4-dichloronitrobenzene, the derivatives 2,4-dichloronitrobenzene chlorinated in the 3-position, the derivatives of 2,4-dichloronitrobenzene chlorinated in the 5-position, and the derivatives of 2,4-dichloronitrobenzene chlorinated in the 3- and 5-positions, with an alkali metal fluoride, in a polar aprotic solvent.

18. A process according to claim 17, wherein the compound or the mixture of compounds of formula (IV) is obtained by reaction of a compound or of a mixture of compounds of formula (V)

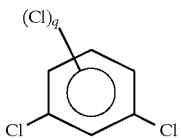
(V)

selected from the group consisting of 1,3-dichlorobenzene, the derivatives of 1,3-dichlorobenzene chlorinated in the 2-position, the derivatives of 1,3-dichlorobenzene chlorinated in the 4-position, and the derivatives of 1,3-dichlorobenzene chlorinated in the 2- and 4-positions, with a reagent for the nitration of aromatic compounds.

19. A process according to claim 1 for the preparation of 3,5-difluoroaniline of formula (Ib):

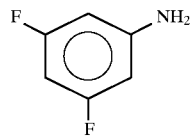
(Ib)

comprising the step of subjecting to catalytic hydrogenation a compound or a mixture of compounds of formula (IIb):

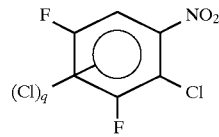
(IIb)

wherein q has a value from 0 to 2, selected from the group consisting of 2-chloro-3,5-difluoronitrobenzene, the derivatives of 2-chloro-3,5-difluoronitrobenzene chlorinated in the 4-position, the derivatives of 2-chloro-3,5-difluoronitrobenzene chlorinated in the 6-position, and the derivatives of 2-chloro-3,5-difluoronitrobenzene chlorinated in the 4- and 6-positions.

20. A process according to claim 19, wherein the compound or the mixture of compounds of formula (IIb) is obtained by reaction of a compound or of a mixture of compounds of formula (VI):

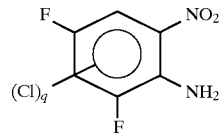
(VI)

selected from the group consisting of 2-amino-3,5-difluoronitrobenzene, the derivatives of 2-amino-3,5-difluoronitrobenzene chlorinated in the 4-position, the derivatives of 2-amino-3,5-difluoronitrobenzene chlorinated in the 6-position, and the derivatives of 2-amino-3,5-difluoronitrobenzene chlorinated in the 4- and 6-positions, with cuprous chloride in the presence of nitrous acid.

21. A process according to claim 20, wherein the compound or the mixture of compounds of formula (VI) is obtained by reaction of a compound or of a mixture of compounds of formula (VII):

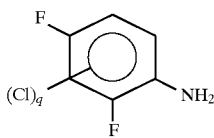
(VIII)

selected from the group consisting of 2,4-difluoroaniline, the derivatives of 2,4-difluoroaniline chlorinated in the 3-position, the derivatives of 2,4-difluoroaniline chlorinated in the 5-position, and the derivatives of 2,4-difluoroaniline chlorinated in the 3- and 5-positions, with a reagent for the nitration of aromatic compounds.

22. A process according to claim 21, wherein the compound or the mixture of compounds of formula (IIb) is obtained by reaction of a compound or of a mixture of compounds of formula (VIII):

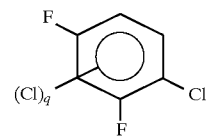
(VIII)

selected from the group consisting of 1-chloro-2,4-difluorobenzene, the derivatives of 1-chloro-2,4-difluorobenzene chlorinated in the 3-position, the derivatives of 1-chloro-2,4-difluorobenzene chlorinated in the 5-position, and the derivatives of 1-chloro-2,4-difluorobenzene chlorinated in the 3- and 5-positions, with a reagent for the nitration of aromatic compounds.

23. A process according to claim 22, wherein the compound or the mixture of compounds of formula (VIII) is obtained by reaction of a compound or of a mixture of compounds of formula (VII):

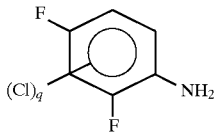
(VII)

selected from the group consisting of 2,4-difluoroaniline, the derivatives of 2,4-difluoroaniline chlorinated in the 3-position, the derivatives of 2,4-difluoroaniline chlorinated in the 5-position, and the the derivatives of 2,4-difluoroaniline chlorinated in in the 3- and 5-positions, with cuprous chloride in the presence of nitrous acid.

24. A process according to claim 22, wherein the compound or the mixture of compounds of formula (VII) is obtained by hydrogenation of a compound or mixture of compounds of formula (IIa):

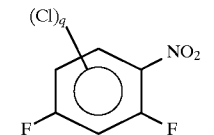
(IIa)

where q has a value from 0 to 2, selected from the group consisting of 2,4-difluoronitrobenzene, the derivatives of 2,4-difluoronitrobenzene chlorinated in the 3-position, the derivatives of 2,4-difluoronitrobenzene chlorinated in the 5-position and the derivatives of 2,4-difluoronitrobenzene chlorinated in the 3- and 5-positions.

* * * * *